United States Patent [19]
Klein et al.

[11] Patent Number: 5,182,215
[45] Date of Patent: Jan. 26, 1993

[54] SCREENING TEST FOR PINEOCYTOMA

[75] Inventors: David C. Klein, Gaithersburg, Md.; Horst W. Korf, Pohlheim, Fed. Rep. of Germany; Jeffrey N. Bruce, Hackensack, N.J.

[73] Assignee: The United States of America as represented by the Department of Health and Human Services, Washington, D.C.

[21] Appl. No.: 368,270

[22] Filed: Jun. 19, 1989

[51] Int. Cl.$^5$ .......................................... G01N 33/558
[52] U.S. Cl. .................................. 436/514; 435/7.92; 435/7.1; 436/64; 436/518; 436/530; 436/813
[58] Field of Search ................ 435/7.1, 7.92; 436/501, 436/64, 813, 514, 518, 530

[56] References Cited
PUBLICATIONS

Korf, et al., *J. Neurosurg.* vol. 70, pp. 682–687 (1989).
Towbin, et al. *J. Immunol. Meth.* vol. 72, pp. 313–340 (1984).
Rollag et al., "Radioimmunoassay of Serum Concentrations of Melatonin in Sheep Exposed to Different Lighting Regimens", *Endo*, vol. 98, No. 2, pp. 482–489 (1976).
Moller et al. "Contrast Enhancement of the Brownish Horseradish Peroxidase-activated 3,3'-Diaminobenzidene Tetrahydrochloride Reaction Product in Black and White Photomicrography by the Use of Interference Filters," *J. Histochem. and Cytochem*, vol. 32, No. 1, pp. 37–42 (1984).
Korf et al., "S–Antigen Immunocytochemistry", *Pineal and Retinal Relationships*, Orlando: Academic Press, pp. 343–355 (1986A).
Korf et al., "S–Antigen-Like Immunoreactivity in a Human Pineocytoma", *ACTA Neuropathol (Berl)*, vol. 69, pp. 165–167 (1986B).
Perentes et al., "S–Antigen immunoreactivity in human pineal glands and pineal parenchymal tumors. A monoclonal antibody study", *ACTA Neuropath (Berl)* vol. 71, pp. 224–227 (1986).
Edwards et al., "Tumor Markers and Cytologic Features of Cerebrospinal Fluid", *Cancer*, vol. 56, No. 7, pp. 1773–1777 (1985).
Korf et al., "Immunocytochemical Evidence of Molecular Photoreceptor Markers in Cerebellar Medulloblastomas," *Cancer*, vol. 60, pp. 1763–1776 (1987).
Vorkapic et al., "Serum Melatonin Levels: A New Neurodiagnostic Tool in Pineal Region Tumors?", *Neurosurgery*, vol. 21, No. 6, pp. 817–824 (1987).
Donoso et al., "Retinal S–Antigen and Retinoblastoma: A Monoclonal Antibody and Flow Cytometric Study", *Invest. Ophthamol. Vis. Sci.*, vol. 26, pp. 568–572 (1985).
Korf et al., "Immunocytochemical demonstration of retinal S–antigen in the pineal organ of four mammalian species", *Cell Tissue Research*, vo. 239, pp. 81–85 (1985).
Bradford, "A Rapid and Sensitive Method for the Quantitation of Microgram Quantities of Protein Utilizing the Principle of Protein–Dye Binding," *Anal. Biochem*, vol. 72, pp. 247–254 (1976).
Kapor et al., "Affinity Purification of Antibodies of Regulatory Subunits of cAMP-Dependent Protein Kinase Using Cross-Linked Immunoabsorbent", *J. Immunol. Meth.*, vol. 57, pp. 215–220 (1983).

*Primary Examiner*—Esther L. Kepplinger
*Assistant Examiner*—Susan C. Wolski
*Attorney, Agent, or Firm*—Cushman, Darby & Cushman

[57] ABSTRACT

A novel method of diagnosing pineal cell tumors by detecting S-antigen in CSF is described.

2 Claims, 2 Drawing Sheets

SCREENING TEST FOR PINEOCYTOMA

The present invention is related generally to the field of diagnostic techniques. More particularly, the present invention is related to a method for differentiating pineal cell tumors from other tumors of the pineal region.

It is currently impossible to differentiate tumors of the pineal region prior to surgery. This group of tumors is heterogenous with respect to histogenesis, origin and biology, and can be subdivided into four distinct groups: (a) tumors of germ cell origin; (b) pineocytomas; (c) tumors of glial and other cell origin; and (d) non-neoplastic cysts and masses. Preoperative characterization of these tumors could improve treatment strategy. Thus, a panoply of markers for each type of pineal region tumor would be of obvious value.

Presently, it appears that there are several potential markers of germ cell tumors, including serum and CSF alpha-fetoprotein and human chorionic gonadotrophin (Edwards et al, Cancer 56: 1773–1777, 1985). In the case of pineoblastoma and pineocytoma, limited study has indicated that these tumors contain hydroxyindole-O-methyltransferase, but that there is an inconsistent occurrence of elevated levels of serum melatonin in patients with these tumors (Arendt, J., Br. J. Med. 2:635–636, 1978; Vorkapic et al, Neurosurgery 21: 817–834, 1987).

S-antigen, which is also known as the 48 kDa protein or arrestin, is an unusual protein originally found in retinal photoreceptors and pinealocytes (Korf et al, Pineal and Retinal Relationships Orlando: Academic Press 1986, pp 343–355; Perentes et al., Acta Neuropath (Berl) 71: 224–227, 1986; Vorkapic et al, Neurosurgery 21:817–824, 1987) and has never been identified in any other non-neoplastic cell type. This protein appears to function in phototransduction in the retina, and probably in photosensory pineal organs of lower vertebrates; the function of this protein in the mammalian pineal has not been established. In addition to being identified in the mammalian pineal and retina, the S-antigen has also been identified in some neoplastic cells of retinoblastoma (Donoso et al, Invest. Ophtalmol. Vis. Sci. 26: 568–572, 1985), pineocytoma or pineoblastoma (Korf et al, Acta Neuropath. (Berl) 69: 165–167, 1986; Perentes et al, Acta Neuropath (Berl) 71:224–227, 1986) and cerebellar medulloblastoma (Korf et al, Cancer 60: 1763–1766, 1987). The presence of this protein in tumors of pineal parenchyma raises the possibility that the S-antigen might be also found in the CSF and that the demonstration of this protein in CSF could serve as a useful diagnostic test to preoperatively identify pineal parenchymal tumors.

SUMMARY OF THE INVENTION

It is, therefore, an object of the present invention to demonstrate the presence of S-antigen in the cerebrospinal fluid (CSF) as a marker of pineal parenchymal tumors in humans.

It is a further object of the present invention to provide a diagnostic test for differentiating pineal cell tumors from other tumors of the pineal region.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
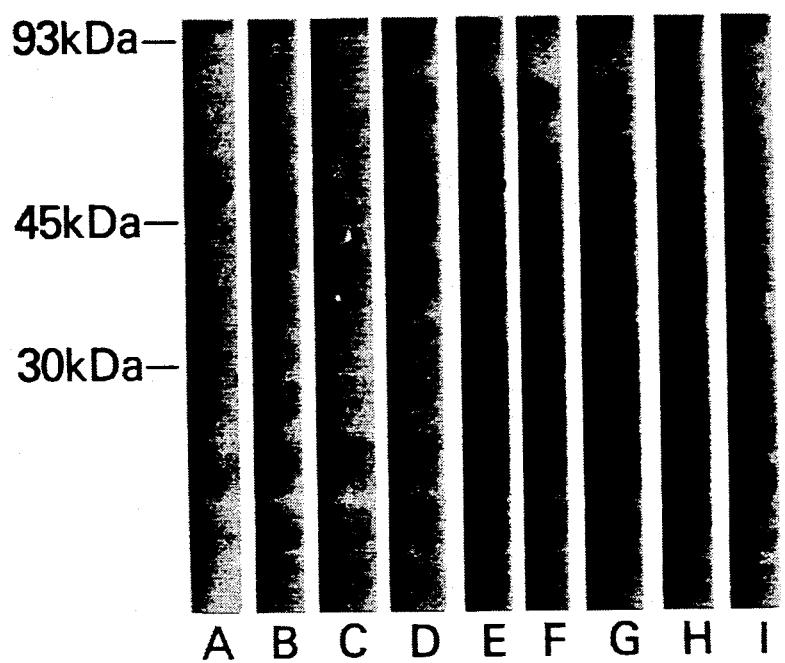
FIG. 1 shows immunoblots of 10% SDS-PAGE of proteins in CSF and tumor homogenates; image enhancement was used to produce contrast required for reproduction. Lane A: Immunoreactive band of approximately 48–50 kDa molecular weight detected in CSF of case No. 3 by use of whole antiserum NEI-04111083. Lane B, C, D: Western blot of CSF of cases No. 1, 2 and 6. Following incubation with whole antiserum NEI-04111083 no immunoreactive protein band was detected. Lane E: Immunoreactive band of approximately 48–50 kDa molecular weight detected in case No. 3 by use of immunopurified antibody. Lane F: After preadsorption of the antiserum with purified S-antigen, this band is no longer detectable. 40 $\mu$l of CSF were applied to each lane. Lanes G, H, I: Western blots of tumor homogenates of case No. 3, 1 and 2 incubated with purified S-antigen antibody. Immunoreactive band of approximately 48–50 kDa molecular weight was detected only in tumor homogenate of case No. 3. Molecular weights were estimated with the use of prestained standard proteins (Amersham).

The above and various other objects and advantages of the present invention are achieved by a diagnostic test for pineal cell tumors, comprising obtaining cerebrospinal fluid from an individual suspected of having pineal cell tumor and determining the presence of S-antigen in the cerebrospinal fluid by conventional methodology, the presence of S-antigen in the CSF being indicative of pineal cell tumor in the individual from whom said cerebrospinal fluid was obtained.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

MATERIALS AND METHODS

CSF samples were obtained from 15 patients admitted to the Neurological Institute, Dept. of Neurosurgery, College of Physicians and Surgeons of Columbia University, New York City, between 1985 and 1987. The samples were stored frozen at −70° C. until examined. Thirteen patients had a tumor of the pineal region; 2 patients displayed hydrocephalic symptoms not caused by a pineal region tumor (Table 1). Frozen samples of tumor tissue were available from 4 patients; formalin-fixed, paraffin-embedded tumor material was obtained from all 13 patients with pineal region tumors.

Immunochemical Demonstration of S-antigen

CSF samples were mixed with sample buffer (2.5 ml 0.25M Tris-HC1 buffer; 4.0 ml 10% SDS, 2.0 ml glycerol; 400 µl bromphenol blue; 100 µl pyronine; 1 ml mercaptoethanol). In additional samples, proteins were first precipitated with trichloracetic acid (TCA, 20%) and resuspended in sample buffer. Fresh frozen tumor tissue was sonicated in ice cold phosphate-buffered saline (PBS), centrifuged at 1000 g for 5 min and the supernatant resuspended in sample buffer. Protein content of CSF and tumor homogenates was determined according to Bradford (Anal. Biochem. 72: 248-254, 1976)

All samples were boiled for 3 min in sample buffer, applied to a 1.5 mm thick 10% SDS-polyacrylamide gel and then electrophoresed by standard techniques. Proteins were then blotted onto nitrocellulose (overnight, 180 mAmp).

S-antigen was detected by means of three rabbit antibovine S-antigen sera: two whole polyclonal antisera (NEI-04111083 and NEI-Z02032085 obtained from National Eye Institute, Bethsda, MD.) and one immunopurified S-antigen antiserum. The latter was prepared according to the method of Kapoor and Cho-Chung (J. Immunol. Meth. 57: 215-220, 1983). In brief, highly purified S-antigen was coupled to CnBr-activated sepharose and mixed with glutaraldehyde. The antiserum was treated by ammonium sulfate precipitation, shaken with the S-antigen-linked SEPHAROSE and transferred into a column. The purified antiserum was eluted from the column by acetic acid and neutralized with Tris buffer. The O.D. was read at 280; finally, the antiserum was dialyzed overnight in PBS. S-antigen was detected by incubating the nitrocellulose sheets for 6 to 24 h in the primary antiserum diluted 1:8000 (whole antisera) or 1:2000 (immunopurified antibody). Affinity purified, peroxidase labeled goat anti-rabbit IgG (H+L, kpl, Gaithersburg, MD) was used as second antibody. Color was developed with either 3'3 diaminobenzidine tetrahydrochloride or 4 chloro-1-naphthol.

To control for unspecific binding of the whole antisera, Western blots of CSF and tumor homogenates were incubated with antisera which had previously been adsorbed with highly purified bovine S-antigen. Highly purified S-antigen was prepared according to the method of Zigler et al (Invest Ophthalmol Vis Sci. 259: 77-81, 1984), separated by means of SDS-PAGE and transferred onto nitrocellulose. The Western blots were cut into several strips. After immunochemical localization of the S-antigen band on selected strips, this region was cut out of the remaining strips and incubated with the whole antisera. Preadsorption was finally controlled by incubating additional Western blots of highly purified S-antigen with these antisera and was considered completed when immunostaining of the S-antigen band could no longer be detected.

Image Enhancement

The blots were photographed with a camera equipped with a DAB interference filter to produce the degree of contrast required for satisfactory reproduction (Moller et al, J. of Histochem. and Cytochem. 32: 37-42, 1983).

Immunocytochemical Demonstration of S-Antigen in Fixed Tumor Tissue

Formalin fixed, paraffin embedded tumor tissue was cut into 5 to 7 µm thick sections. After deparaffinization, sections were incubated with S-antigen antisera for 24 to 48 h at 4° C., washed in PBS containing 0.3% NONIDET P 40 and then incubated with affinity purified, peroxidase labeled goat anti-rabbit IgG (H+L, kpl, Gaithersburg, MD, diluted 1:200) for 2 h. Peroxidase activity was demonstrated by use of either 3'3 diaminobenzidine tetrahydrochloride or 4 chloro-1-naphthol. Immunocytochemical controls were performed as described by Korf et al (Cell Tissue Res. 239: 81-85, 1985) and Korf et al (Acta Neuropath. (Berl) 69: 165-167, 1986).

Radiometric Assay for HIOMT-Activity in Homogenates of Pineal Tumors and Normal Human Pineal Glands Following the procedure described by Sudgen et al (Methods in Enzymology 142. Orlando: Academic Press 1987, pp. 590-596), hydroxyindole-O-methyltransferase (HIOMT) activity was measured in 10 and 20 µl aliquots of four pineal tumor homogenates and 7 normal pineal glands obtained from autopsy.

Melatonin Radioimmunoassay

Melatonin levels in CSF were determined by radioimmunoassay with the use of rabbit anti-melatonin-BSA serum (Rollag et al, Endocrinology 98:482-489, 1976). One hundred µl samples of CSF, or of melatonin standards (0.5-250 pg/100 µl) were incubated (48 hr, 4° C.) with antiserum (R1055, Sep. 16, 1974) and $^{125}$I-melatonin analog (Hazelton Lab., Vienna, VA) in a final volume of 400 µl. Antibody bound radioactivity was precipitated by adding 2.5 ml of 95% ethanol (4° C.) and collected by centrifugation (100 g, 30 min, 4° C.). Radioactivity was measured in the precipitate. The amount of melatonin was calculated from a 4 parameter logistic function fitting the counts observed in tubes containing standard solutions to pg melatonin originally added.

RESULTS

CSF samples and tissue obtained during surgical removal of tumors from 13 patients suffering from pineal region tumors were analyzed. The tumors were characterized according to neurohistopathological criteria as pineocytoma (n=1), germinoma (n=1), ependymoma (n=4), meningioma (n=1), low grade astrocytoma (n=2), embryonal cell carcinoma (n=1), hamartoma (n=1), adenocarcinoma (n=1) and metastatic esophageal carcinoma (n=1) (Table 1).

A. CSF Analysis

As shown by the Western blot technique, the CSF of the patient with a pineocytoma contained a 48-50 kDa protein which was immunopositive with whole and immunopurified antisera (FIG. 1). Immunoreactivity was abolished after the antisera were preadsorbed with highly purified bovine S-antigen (FIG. 1). This protein could not be detected in the CSF of the other patients studied (Table 1; FIG. 1). The CSF of the pineocytoma patient also had >3-fold elevated daytime melatonin levels as compared to other day time CSF samples tested (148 versus 8 to 45 pg/ml, Table 1).

B. Analysis of Tumor Biopsies

Figure 2A:
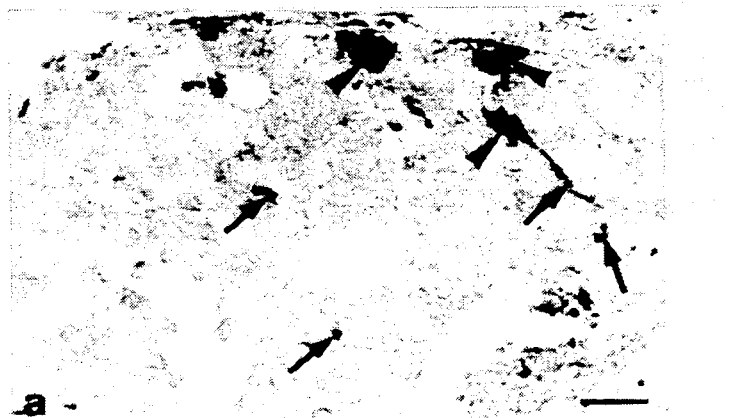
FIG. 2 is an immunocytochemical demonstration of S-antigen immunoreactive tumor cells in pineocytoma (case No. 3) and normal pineal tissue (case No. 8). a: S-antigen immunoreactive tumor cells of the pineocytoma (arrowheads) are scattered between immunonegative tumor cells. Beaded processes (arrows). b: No immunoreactive cells are found in an adjacent section incubated with the preadsorbed antibody. c: Normal S-antigen immunoreactive pinealocytes (arrowheads) give rise to beaded processes (arrows) a–c$\times$330; bars-30 $\mu$M.
Figure 2B:
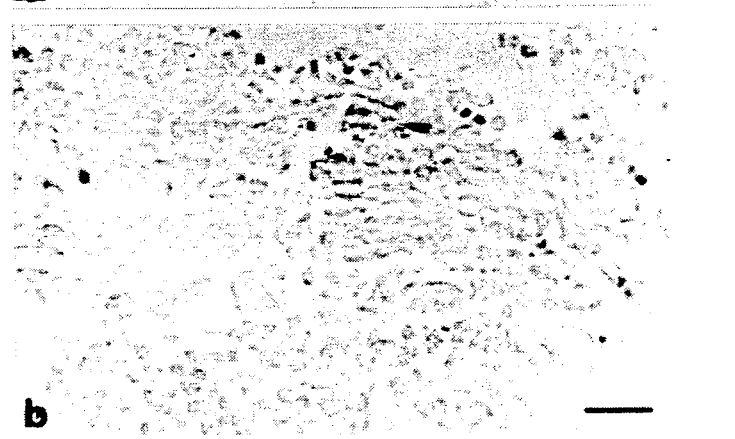
Figure 2C:

Immunocytochemical investigations of paraffin sections revealed a few S-antigen immunorective tumor cells in the pineocytoma. These cells were scattered among immunonegative neoplastic cells forming the major portion of the pineocytoma (FIG. 2a). S-antigen immunorectivity was found in the perikarya and occasionally also in cell processes of beaded appearance. Immunoreactivity was absent when preadsorbed primary antisera were used. S-antigen immunorective tumor cells were not found in the other tumors. However, the biopsy of case No. 8 included a piece of normal pineal gland with S-antigen immunoreactive pinealocytes (FIG. 2c). It was observed that the size number and distribution of S-antigen immunoreactive pinealocytes closely resembled those of S-antigen immunoreactive tumor cells of the pineocytoma (case No. 3; FIG. 2a).

Western blot analysis was performed with homogenates of fresh frozed biopsy samples of the pineocytoma (case No. 3); germinoma (case No. 2), ependymoma (case No. 1) and embryonal cell carcinoma (case No. 6). This revealed that a 48-50 kDa protein immunoreactive to all three S-antigen antisera was present in the pineocytoma (FIG. 1), but was absent from the germinoma, ependymoma and embryonal cell carcinoma.

It was also found that HIOMT activity was present in the pineocytoma homogenate, but absent in the other 3 tumors tested (Table 2). It should be noted that none of the tumor homogenates contained normal pineal tissue and that HIOMT activity in the pineocytoma was about 25% (1.0 nmol/mg protein/h) that in normal human pineal glands obtained at autopsy (4.3±1.5 nmol/mg protein/h).

The results presented herein from 13 patients with different pineal region tumors clearly demonstrate that the detection of a 48 kDa S-antigen immunoreactive protein in the CSF is a positive indicator of the presence of pineocytoma. This finding also provides a valuable diagnostic tool for preoperatively differentiating these neoplasms from other types of pineal region tumors.

This conclusion is based on the finding that such a protein is present only in the CSF of the patient with pineocytoma and not found in the CSF of 12 patients with other types of pineal region tumors. That the protein detected in the CSF of the pineocytoma patient is authentic S-antigen is confirmed by the following tests: (1) the immunoreactive material behaved as a 48 kDa protein in SDS-PAGE, (2) the protein reacted with three different S-antigen antisera; and (3) it did not bind to the antiserum preadsorbed with authentic bovine S-antigen.

The immunochemical findings in the CSF also correlated well with immunocytochemical results obtained from the corresponding tumor biopsies. S-antigen immunoreactive tumor cells were exclusively found in the pineocytoma removed from the patient whose preoperative CSF contained S-antigen. The correlation of immunochemical and immunocytochemical results indicate that the S-antigen in the CSF is derived from neoplastic cells rather than from normal S-antigen immunoreactive pinealocytes destructed by neoplasmic growth.

Clearly, the presence of S-antigen in the CSF as a reliable indicator of pineal cell tumors obviates the necessity of performing stereotaxic biopsy and is valuable in deciding upon a course of therapy.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

| Case | Age(yrs) | Sex | Neuropathological diagnosis | CSF-analysis time of sampling | protein (mg/ml) | melatonin (pg/ml) | S-antigen |
|---|---|---|---|---|---|---|---|
| 1 | 20 | F | ependymoma | 1000 | 0.25 | 45 | — |
| 2 | 32 | M | germinoma | 1200 | 0.08 | 19 | — |
| 3 | 23 | M | pineocytoma | 1100 | 4.00 | 148 | + |
| 4 | 61 | F | ependymoma | 900 | 0.15 | 18 | — |
| 5 | 29 | M | ependymoma | 1000 | 0.26 | 23 | — |
| 6 | 41 | M | embryonal cell carcinoma | 2100 | 0.48 | 11 | — |
| 7 | 39 | M | hamartoma | 2200 | 0.40 | 13 | — |
| 8 | 27 | F | low grade astrocytoma | 1900 | 2.60 | 50 | — |
| 9 | 48 | M | meningioma | 1800 | 0.82 | 14 | — |
| 10 | 39 | F | ependymoma | 1700 | 0.60 | 19 | — |
| 11 | 59 | M | metastatic esophageal carcinoma | 1600 | 0.54 | 14 | — |
| 12 | 35 | F | low grade astrocytoma | 2300 | 0.16 | 17 | — |
| 13 | 47 | M | adenocarcinoma | 900 | 4.00 | 28 | — |
| 14 | 18 | F | hydrocephalus no tumor | 800 | 0.12 | 25 | — |
| 15 | 9 | F | hydrocephalus no tumor | 1200 | 0.10 | 8 | — |

TABLE 2

Determination of immunoreactive S-antigen and radiometric assay of HIOMT activity in 4 pineal region-tumors*

| Case no** | Neuropathological diagnosis | S-Antigen | HIOMT-activity (nmol/mg protein/h) |
|---|---|---|---|
| 1 | ependymoma | — | n.d. |
| 2 | germinoma | — | n.d. |
| 3 | pineocytoma | + | 0.987 |
| 4 | embryonal cell | — | n.d. |

TABLE 2-continued

Determination of immunoreactive S-antigen and
radiometric assay of HIOMT activity in 4 pineal region-tumors*

| Case no** | Neuropathological diagnosis | S-Antigen | HIOMT-activity (nmol/mg protein/h) |
|---|---|---|---|
| | carcinoma | | |

*Samples collected for this investigation did not contain normal pineal tissue.
**Case nr. corresponds to case nr. in Table 1.
n.d. not detectable

What is claimed is:

1. A screening test for pineocytoma, comprising the steps of:
   a) obtaining cerebrospinal fluid from an individual;
   b) contacting said fluid with an antibody which specifically binds S-antigen, under conditions effective for and a time sufficient for binding of said antibody to said S-antigen to occur;
   c) detecting any S-antigen from said fluid bound to said antibody, the presence of S-antigen in said fluid being indicative of pineocytoma in the individual from whom said cerebrospinal fluid was obtained.

2. A screening test for pineocytoma, comprising the steps of:
   a) obtaining cerebrospinal fluid from an individual;
   b) separating said fluid into components by electrophoresis on a polyacrylamide gel;
   c) transferring said components onto a nitrocellulose filter;
   d) contacting said filter with an antibody which specifically binds S-antigen, under conditions effective for and a time sufficient for binding of said antibody to said S-antigen to occur;
   e) detecting any S-antigen from said filter bound to said antibody, the presence of S-antigen on said filter being indicative of pineocytoma in the individual from whom said cerebrospinal fluid was obtained.

* * * * *